(12) United States Patent
Bierens

(10) Patent No.: US 11,657,908 B2
(45) Date of Patent: May 23, 2023

(54) METHODS AND SYSTEMS FOR HANDLING VIRTUAL 3D OBJECT SURFACE INTERACTION

(71) Applicant: KONINKLIJKE PHILIPS N.V., Eindhoven (NL)

(72) Inventor: Bernardus Petrus Hendrikus Johannus Bierens, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 435 days.

(21) Appl. No.: 16/851,722

(22) Filed: Apr. 17, 2020

(65) Prior Publication Data

US 2020/0335204 A1    Oct. 22, 2020

(30) Foreign Application Priority Data

Apr. 19, 2019  (EP) ...................................... 19170391

(51) Int. Cl.
  *G16H 30/40*  (2018.01)
  *G06T 15/06*  (2011.01)
  *G06T 17/10*  (2006.01)

(52) U.S. Cl.
  CPC ............. *G16H 30/40* (2018.01); *G06T 15/06* (2013.01); *G06T 17/10* (2013.01)

(58) Field of Classification Search
  CPC ......... G06T 15/06; G06T 15/00; G06T 19/00; G06T 2210/41; G06T 7/75; G06T 2200/04; G06V 10/20; G06V 20/64
  See application file for complete search history.

(56) References Cited

U.S. PATENT DOCUMENTS

| | | | |
|---|---|---|---|
| 2008/0096152 A1 | 4/2008 | Cheang et al. | |
| 2014/0278319 A1* | 9/2014 | Thiruvengada | G06F 30/20 703/11 |

(Continued)

OTHER PUBLICATIONS

Lehericey, F. et al., "GPU Ray-Traced Collision Detection for Cloth Simulation", Proceedings of ACM Symposium on Virtual Reality Software and Technology, 2015, Pekin, China. hal-01218186.

(Continued)

*Primary Examiner* — Guillermo M Rivera-Martinez
(74) *Attorney, Agent, or Firm* — Michael W. Haas

(57) ABSTRACT

The invention provides for a means of aligning a first virtual object with a second virtual object that is different from the first virtual object within a scene volume in a 3D virtual space. The method includes performing a 3D scan of the user's head to get the first virtual object. The second virtual object comprises a 3D model of a mask. The method further determining a location of a first surface point on a surface of the first virtual object based on a first ray casting of the first virtual object, and determining a location of a second surface point on a surface of the second virtual object based on a second ray casting of the second virtual object. The second surface point has a desired positional relationship with respect to the first surface point. The first ray casting originates from outside the scene volume and the second ray casting originates from inside the scene volume. A relative position between the location of the first surface point and the location of the second surface point is then determined and the location of the second surface point is adjusted based on the relative position.

11 Claims, 4 Drawing Sheets

(56) References Cited

U.S. PATENT DOCUMENTS

| | | | |
|---|---|---|---|
| 2015/0055085 A1* | 2/2015 | Fonte | G16H 50/50 |
| | | | 700/98 |
| 2015/0157822 A1* | 6/2015 | Karpas | G06V 40/193 |
| | | | 700/98 |
| 2016/0092645 A1* | 3/2016 | Vlutters | G06F 3/0482 |
| | | | 715/771 |
| 2016/0180587 A1* | 6/2016 | Bai | A62B 7/04 |
| | | | 345/419 |
| 2016/0296720 A1* | 10/2016 | Henry | A61M 16/0875 |
| 2018/0147062 A1 | 5/2018 | Ay et al. | |
| 2020/0233239 A1* | 7/2020 | Schwarz | G02C 13/003 |
| 2021/0077763 A1* | 3/2021 | Huddart | A61M 16/0866 |

OTHER PUBLICATIONS

International Search Report for PCT/EP2020/060360 dated Apr. 13, 2020.

* cited by examiner

METHODS AND SYSTEMS FOR HANDLING VIRTUAL 3D OBJECT SURFACE INTERACTION

CROSS-REFERENCE TO PRIOR APPLICATIONS

This application claims the priority benefit under 35 U.S.C. § 119(e) of European Patent Application No. 19170391.7, filed on Apr. 19, 2019, the contents of which are herein incorporated by reference.

FIELD OF THE INVENTION

The invention relates to the field of 3D digital imaging, and more specifically to the field of surface interactions between 3D digital objects.

BACKGROUND OF THE INVENTION

It is often helpful to visualize the interaction between two objects in digital space before implementing a change in the real world.

For example, a system for visualizing the fit of a piece of medical apparatus to a subject's body may allow a user to easily and objectively prescribe the optimal medical apparatus to the subject.

FIG. 1 shows such an example, where a model of a user's head 100 is shown in combination with a respiratory mask 110.

In this case, a subject may be able to view a 3D model of their head, fitted with a respiration mask that they have selected. The shape of the 3D model of the mask has to be adjusted to fit the 3D facial scan in order to accommodate the individual face shape of any given subject. Current algorithms typically place the mask correctly over the facial scan surface; however, there often appear gaps between the face and the mask or the mask disappears partially below the facial surface (as shown by region 120). This is unappealing to the subject and may mislead the clinician into selecting a mask with an inappropriate fit.

Francois Lehericey et al: "Extended version: GPU Ray-Traced Collision Detection for Cloth Simulation", Nov. 2, 2015 pages 1-9, XP055638417, the open archive Hal, discloses a method for performing collision detection with cloths with ray-tracing at an interactive frame-rate.

SUMMARY OF THE INVENTION

The invention is defined by the claims.

According to examples in accordance with an aspect of the invention, there is provided a method for aligning a first virtual object with a second virtual object, wherein the second virtual object is different from the first virtual object, within a scene volume in a 3D virtual space, the method comprising:

performing a 3D scan of the user's head, wherein the first virtual object comprises the 3D scan of the user's head, and wherein the second virtual object comprises a 3D model of a mask;

determining a location of a first surface point on a surface of the first virtual object based on a first ray casting of the first virtual object, wherein the first ray casting is in a direction from outside the scene volume towards the inside of the scene volume;

determining a location of a second surface point on a surface of the second virtual object based on a second ray casting of the second virtual object, wherein the second ray casting is in a direction from inside the scene volume to outside the scene volume, and wherein the second surface point has a desired positional relationship with respect to the first surface point, wherein the desired spatial relationship the inner surface of the 3D model of the mask sits flush with the surface of the 3D model of the user's head;

determining a relative position between the location of the first surface point and the location of the second surface point; and adjusting the location of the second surface point based on the relative position. The method provides for a means of aligning a second virtual object with a first virtual object and for adjusting the surface of the second virtual object according to its position relative to the first virtual object.

The method may provide for a means of preventing the surface of the second virtual object penetrating the surface of the first virtual object in examples where collision may otherwise occur.

By performing the ray casting of the first object from outside the scene and the ray casting of the second object from within the scene, it is possible to obtain a detailed view of the surfaces of the objects that will be interacting with each other and therefore require adjustment.

By using a 3D scan of a user's head and a 3D model of a mask, an individual representation of a given user's head may be obtained and the relationship between a mask and a user's face may be determined virtually. In this case, the method provides for a means of visualizing how a mask may fit an individual user without parts of the mask erroneously colliding, and clipping through, the 3D scan of the user.

In an embodiment, adjusting the location of the second surface point comprises adjusting the location of the second virtual object.

In this way, the entire second virtual object may be shifted in order to obtain the desired positional relationship between the first surface point and the second surface point.

In an embodiment, the steps of the method are repeated for a plurality of surface points on the first virtual object and a corresponding plurality of surface points on the second virtual object.

In this way, the entire surface of the second virtual object may be adjusted based on its spatial relationship with the surface of the first virtual object.

In a further embodiment, adjusting the location of the second surface point comprises deforming the second virtual object based on the adjusted location of the second surface point.

In this way, the shape of the second virtual object may be changed in order to accommodate the desired interaction with the first virtual object.

In a further embodiment, deforming the second virtual object comprises adjusting a location of an additional second surface point based on the adjusted location of the second surface point of the plurality of second surface points.

In this way, when a given surface point of the second virtual object is moved, adjacent surface points may also be moved in order to provide a smooth transition along the surface of the second virtual object when undergoing deformation.

In a further embodiment, the 3D model of a mask comprises one or more of:

a CPAP mask;
a medical sensory device;
a hearing aid;

a neck brace;
a piece of dental equipment, such as braces;
a piece of eyewear, such as glasses;
a pair of headphones;
a virtual reality headset;
a visualization of a post operation scar; and
an implant.

In an embodiment, the method comprises performing a preliminary alignment of the first virtual object and the second virtual object.

In this way, the first and second virtual objects may be brought substantially into the correct positions before the detailed adjustment of the surface of the second object is performed.

In an embodiment, the method further comprises:
deforming the first virtual object; and
deforming the second virtual object based on the deformation of the first virtual object.

In this way, the effects of a deformation of the first virtual object on the second virtual object may be modelled.

According to examples in accordance with an aspect of the invention, there is provided a computer program comprising computer program code means which is adapted, when said computer program is run on a computer, to implement the methods described above.

According to examples in accordance with an aspect of the invention, there is provided a system for aligning a first virtual object with a second virtual object, wherein the second virtual object is different from the first virtual object, within a scene volume in a 3D virtual space, the system comprising:
a scanner adapted to generate a 3D model of a user's head based on a scan of the user's head; and
a processor adapted to:
receive the 3D model of the user's head from the scanner as the first virtual object, and wherein the second virtual object comprises a 3D model of a mask;
determine a location of a first surface point on a surface of the first virtual object based on a first ray casting of the first virtual object, wherein the first ray casting is in a direction from outside the scene volume towards the inside of the scene volume;
determine a location of a second surface point on a surface of the second virtual object based on a second ray casting of the second virtual object, wherein the second ray casting is in a direction from inside the scene volume to outside the scene volume and wherein the second surface point has a desired positional relationship with respect to the first surface point, wherein the desired spatial relationship the inner surface of the 3D model of the mask sits flush with the surface of the 3D model of the user's head; determine a relative position between the location of the first surface point and the location of the second surface point; and adjust the location of the second surface point based on the relative position.

In an embodiment, the system further comprises a display adapted to display the scene volume to a user.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
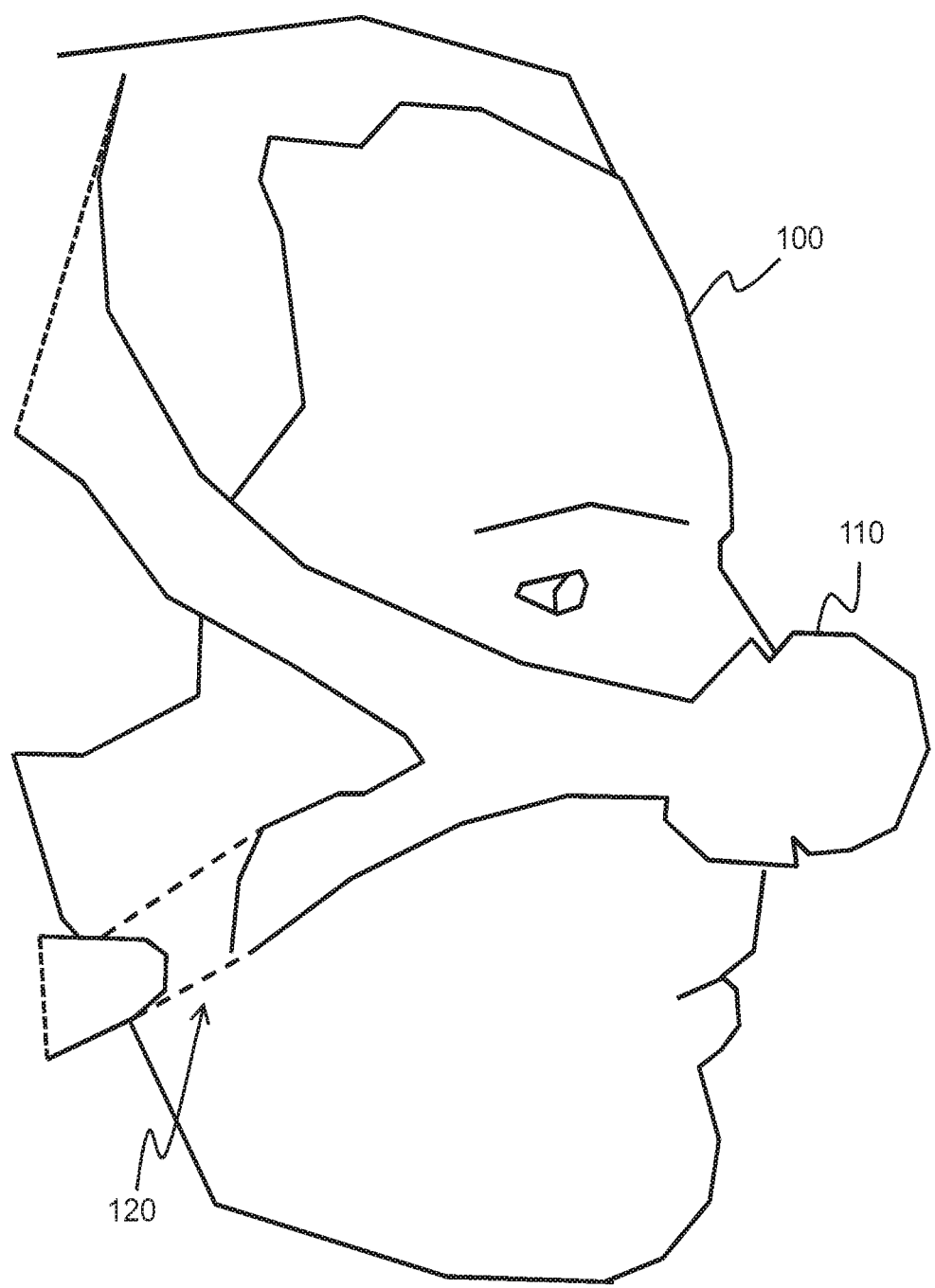
FIG. 1 shows a graphical representation of the prior art.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides for a means of aligning a first virtual object with a second virtual object, wherein the second virtual object is different from the first virtual object, within a scene volume in a 3D virtual space. The method includes performing a 3D scan of the user's head, wherein the first virtual object comprises the 3D scan of the user's head, and wherein the second virtual object comprises a 3D model of a mask. The method further includes determining a location of a first surface point on a surface of the first virtual object based on a first ray casting of the first virtual object. The method further includes determining a location of a second surface point on a surface of the second virtual object based on a second ray casting of the second virtual object, wherein the second surface point has a desired positional relationship with respect to the first surface point, wherein the desired spatial relationship the inner surface of the 3D model of the mask sits flush with the surface of the 3D model of the user's head. The first ray casting originates from outside the scene volume and the second ray casting originates from inside the scene volume. A relative position between the location of the first surface point and the location of the second surface point is then determined and the location of the second surface point is adjusted based on the relative position.

Figure 2:
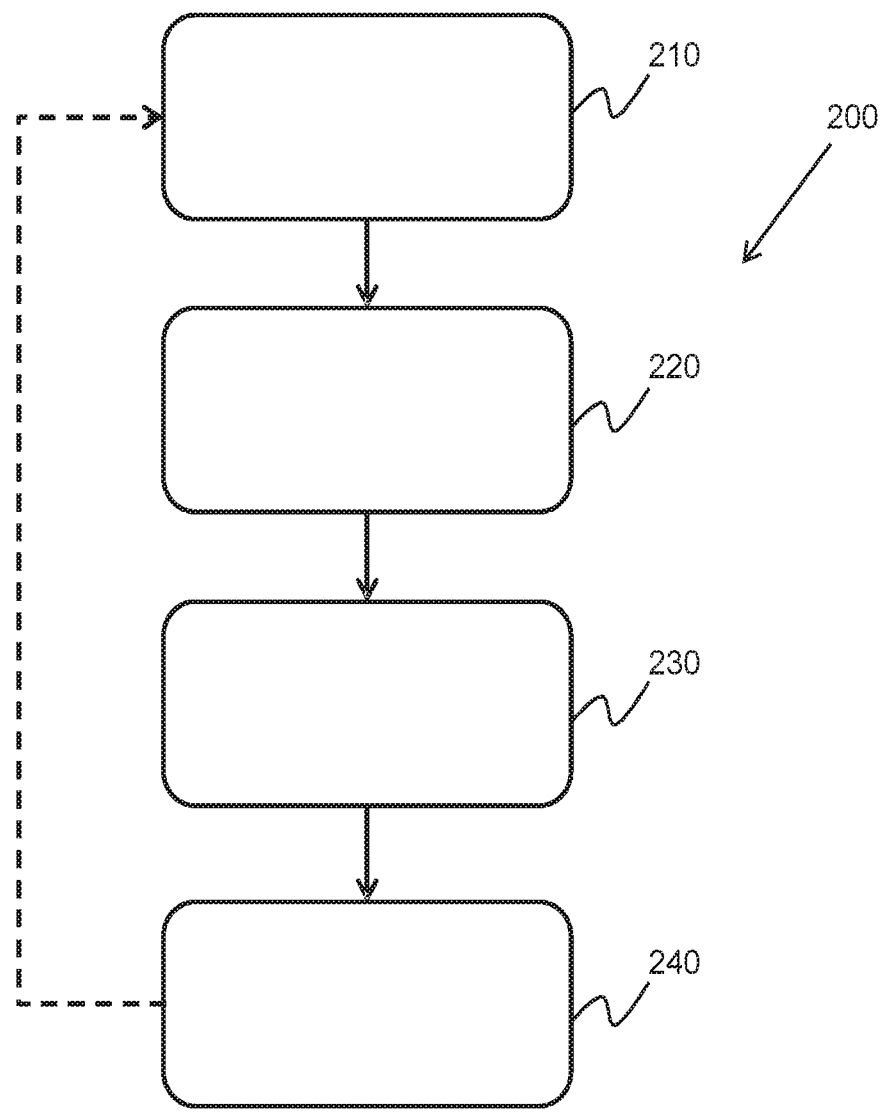
FIG. 2 shows a method of the invention.

FIG. 2 shows a method 200 for aligning a first virtual object with a second virtual object within a scene volume in a 3D virtual space.

The method begins in step 210 by determining a location of a first surface point on a surface of the first virtual object based on a first ray casting of the first virtual object. The first ray casting originates from outside the scene volume.

In step 220, a location of a second surface point on a surface of the second virtual object is determined based on a second ray casting of the second virtual object and wherein the second surface point has a desired positional relationship with respect to the first surface point. The second ray casting originates from inside the scene volume.

In other words, the locations of two surface points, having a desired spatial relationship to each, on the surfaces of separate virtual objects are determined using ray casting. The ray casting technique is described further below with reference to FIG. 3.

In step 230, a relative position between the location of the first surface point and the location of the second surface point is determined.

In step 240, the location of the second surface point is adjusted based on the relative position.

By way of example, the first virtual object may be a 3D scan of a user's head, in which case the method may also include performing the 3D scan of the user's head, and the second virtual object may be a 3D model of a mask. The 3D model of a mask may include a CPAP mask, or any other type of mask adapted to be worn by the user.

In this example, the method may be employed to adjust the inner surface of the mask in order to match the surface of the users face. In this way, the visual clipping shown in FIG. 1, wherein the mask passes through the face of the user, may be avoided.

For example, the location of the second surface point may be adjusted by adjusting the location of the second virtual object. In other words, the entire second virtual object may be translated to adjust the position of the second surface point. In the example outlined above, the location of the entire 3D model of the mask may be adjusted about the 3D model of the user's head.

Alternatively, the steps of the above method 200 may be repeated for a plurality of surface points on the first virtual object and a corresponding plurality of surface points on the second virtual object.

In other words, for complex objects having multiple interacting surface points, the method may be applied across any number of surface points in order to suitably align the first virtual object and the second virtual object.

Returning to the example of the 3D model of the user's head and the 3D model of the mask, a number of surface points along the mask may be adjusted according to their relationship to the corresponding surface points on the user's face. In this way, the entire mask may be adjusted in a detailed manner to show an exact fit of the mask to the user's face.

Further, adjusting the location of the second surface point may include deforming the second virtual object based on the adjusted location of the second surface point, or the adjusted location of the plurality of surface points.

For example, where the second virtual object comprises a wireframe joining each of the second surface points, additional second surface points may be generated along a given wire in order to allow for a smooth transition along the surface of the second virtual object. Further, when deforming the second virtual object, the location of such an additional second surface point may be adjusted based on the adjusted location of the second surface point of the plurality of second surface points.

In other words, as the initial second surface point is moved, an additional adjacent second surface may be moved by an appropriate amount, such that the integrity of the surface of the second virtual object is maintained within the 3D space.

In the above example, this may be visualized as the mask stretching to fit an individual user's face. In this way, individualized representations of fit may be provided to each user, rather than providing a standardized view that may not accurately represent how the mask will fit in reality.

In addition, the method may allow for the simulation of an interaction between the first virtual object and the second virtual object. For example, the first virtual object may undergo a deformation, in which case the second virtual object may then be deformed based on the deformation of the first virtual object.

For example, the 3D model of the user's head may be animated to simulate speech or a yawn. In response to this, the 3D model of the mask may be deformed accordingly, in order to visualize how the mask will function during everyday use.

Further, the second virtual object may be programed to obey certain predetermined limitations, for example, relating to material properties. For example, in the case of the second virtual object being a mask, a measure of flexibility may be assigned to the mask according to the material it is constructed from. In this case, if the adjustment of the second surface point exceeds a flexibility threshold in order to accommodate the 3D model of the user's head, an alert may be generated informing the user that the selected mask may not be suitable for the given user.

It should be noted that a preliminary alignment of the first virtual object and the second virtual object may be performed before the method begins. Large adjustments may be performed during the preliminary alignment; whereas, the method described above may be reserved for more detailed adjustments of the second surface point.

In further examples, the first virtual object and second virtual object may be any 3D model of two objects whose interactions require investigation. For example, the first virtual object may be a 3D model of the user's head and the second virtual object may be a 3D model of one or more of: a hearing aid; a piece of eyewear, such as glasses; a neck brace; a piece of dental equipment, such as braces; a visualization of a post operation scar; an implant; and the like.

Further, the first virtual object may be a 3D model of any body part of a user and the second virtual object may be a 3D model of any piece of equipment or visualization adapted to interact with said body part.

Figure 3A:
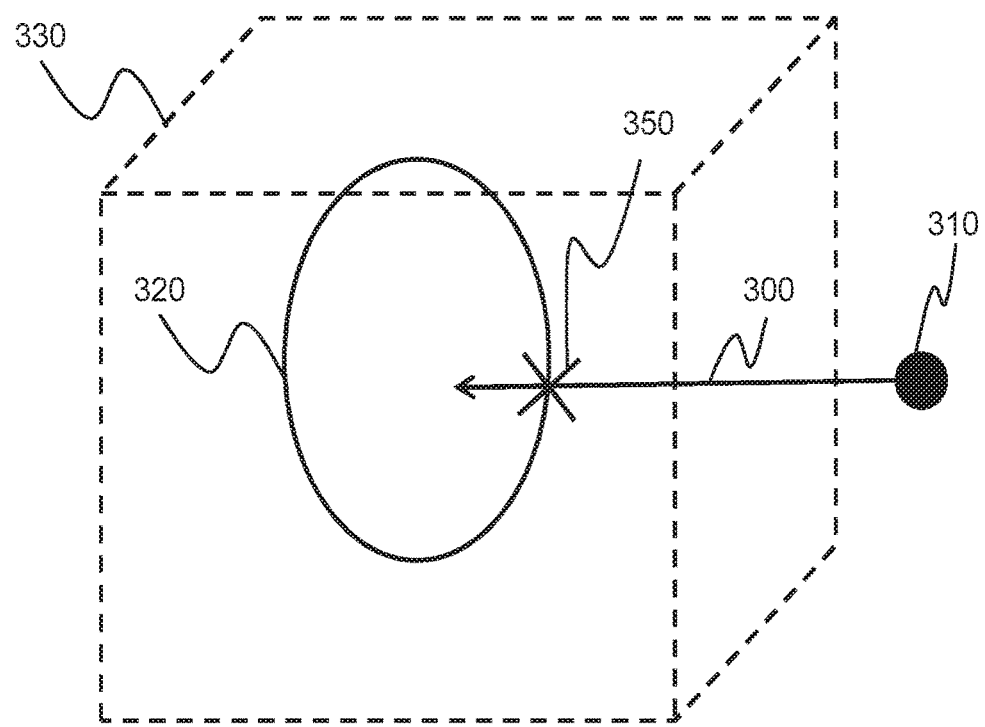
FIGS. 3a and 3b show a schematic representation of the ray casting of the method of FIG. 2.
Figure 3B:
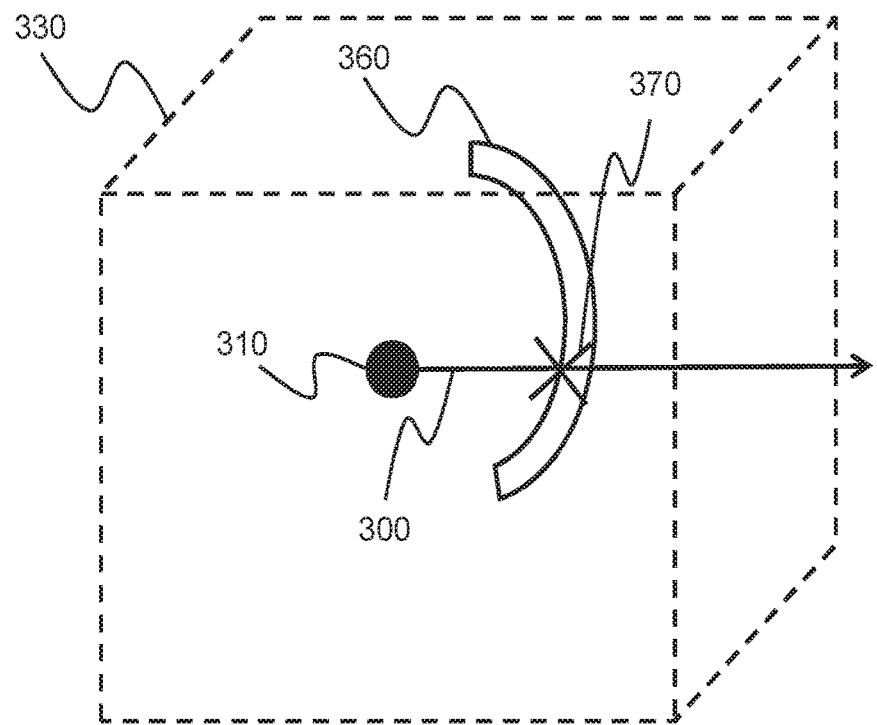

FIGS. 3a and 3b show a graphical representation of the ray casting methods discussed above.

Ray casting refers to the use of ray-surface intersection tests in computer graphics and computational geometry. For example, ray casting may be used to address the general problem of determining the first object in a scene to be intersected by a ray or in a direct volume rendering method, in which the ray is pushed through a virtual object and the 3D scalar field of interest is samples along the ray inside the object.

Ray casting is a computer graphics rendering algorithm based on the geometric algorithm of ray tracing. Ray tracing-based rendering algorithms operate in image order to render 3D scenes into 2D images.

The speed and simplicity of ray casting comes from computing the color of the light without recursively tracing additional rays that sample the radiance incident on the point that the ray hits.

In nature, a light source emits a ray of light that travels, eventually, to a surface that interrupts its progress. At this point, any combination of three things may happen with this light ray: absorption, reflection, and refraction. The surface may reflect all, or part, of the light ray in one or more directions. It may also absorb part of the light ray, resulting in a loss of intensity of the reflected and/or refracted light. If the surface has any transparent or translucent properties, it refracts a portion of the light beam into itself in a different direction while absorbing some (or all) of the spectrum (and possibly altering the color). Between absorption, reflection, and refraction, all of the incoming light must be accounted for, and no more. A surface cannot, for instance, reflect 66% of an incoming light ray, and refract 50%, since the two would add up to be 116%. From here, the reflected and/or refracted rays may strike other surfaces, where their absorptive, refractive, and reflective properties are again calculated based on the incoming rays. Some of these rays travel in such a way that they hit the eye 310, contributing to the final rendered image.

In the virtual space, there is no need to simulate the lighting of a scene in this way. Rather, the geometric ray may be traced directly from the eye, such that only rays that would contribute to the rendered image are simulated.

In operation, and looking to FIG. 3a showing the first ray casting operation of the method as an example, a geometric ray 300 is traced from the eye of the observer 310 to the first virtual object 320 from outside of the scene volume 330. The geometric ray is used to sample the virtual light that would be travelling toward the observer from the ray direction. In FIG. 3a, the geometric ray strikes the first virtual object at the first surface point 350.

FIG. 3b shows a graphical representation of the second ray casting operation, which is performed within the scene volume 330. In this instance, the geometric ray 300 is traced from the eye 310 to the second virtual object 360. The geometric ray strikes the second virtual object at the second surface point 370.

The scene volume is defined as the 3D virtual space in which the first 3D virtual object and the second 3D virtual object exist. It defines the coordinate system which gives the virtual objects their locations. In addition, the scene volume also contains other components common in 3D computer graphics, such as: cameras; light sources; background decorations; and the like. The scene volume may take any shape appropriate for the given implementation. The scene volume may be defined by the minimum 3D volume required to encompass the first and second 3D virtual objects, or any other shape or size of 3D volume that may encompass the 3D virtual objects.

A ray, such as a geometric ray 300, is a straight line through the 3D scene volume. A collision check can be applied to this straight line (ray cast) in one of two directions along the line.

In the method described above, the ray casting is performed along the rays in both directions, once (the first ray casting) to collide with the first 3D virtual object, and another time (the second ray casting) to collide with the second 3D virtual object. This means that the first ray cast travels along the ray from the outside of the scene volume towards the center of the scene, where the first and second virtual objects are located; whereas, the second ray cast travels in the opposite direction, i.e. from within the scene volume directed away from the center.

When the placement of a first 3D model in relation to a second 3D model is constrained by, for example, anatomical aspects such as a 3D model of a respiration mask that must go over the nose, rather than over the chin, then traditional placement methods may work correctly when dealing with known, pre-defined 3D model shapes.

However, when one or more of the 3D model shapes are not known ahead of time, for example, because they are created on-site by a user using a scanner, such as a 3D model of a user's head, the multi-stage ray casting technique described above provides a system that may both consider the anatomical aspects and be flexible enough to respond to shapes varying across the usage time of the system.

From the known location of the eye in the first ray casting operation and the second ray casting operation, and the properties of the geometric ray in each case, the locations of the first surface point and the second surface point within the scene volume may be determined.

The relative locations of the surface points may be compared to the desired spatial relationship between them. For example, in the case shown in FIG. 1, one or more surface point of the 3D model of the mask will be shown as encroaching on the 3D model of the user's head, meaning that the desired spatial relationship is not satisfied. The desired spatial relationship in this case may be that the inner surface of the 3D model of the mask sits flush with the surface of the 3D model of the user's head.

Figure 4:
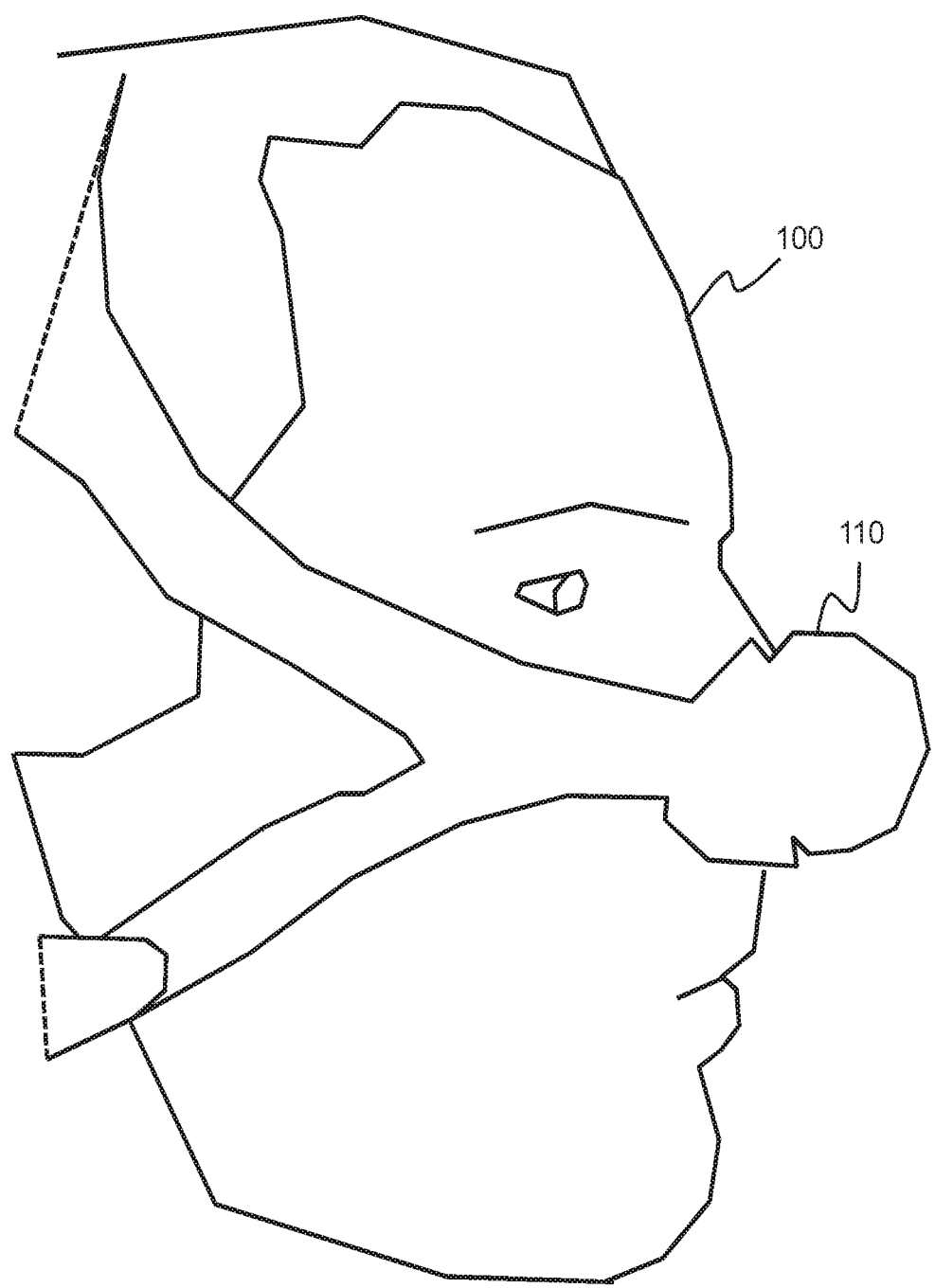
FIG. 4 shows a graphical representation of an implementation of the method of FIG. 2.

FIG. 4 shows an updated version of the scenario of FIG. 1 after the methods described above have been applied. As can be seen from FIG. 4, the second virtual object, the mask 110, has been adjusted according the first virtual object, the user's head 100, such that there are no longer any regions of erroneous encroachment between the two virtual objects.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method for aligning a first virtual object with a second virtual object, wherein the second virtual object is different from the first virtual object, within a scene volume in a three dimensional (3D) virtual space in which the first 3D virtual object and the second 3D virtual object exist and which defines a coordinate system that gives each of the virtual objects their locations, the method comprising:
performing a 3D scan of a user's head, wherein the first virtual object comprises the 3D scan of the user's head, and wherein the second virtual object comprises a 3D model of a mask to be worn by the user;
determining a location of a first surface point on a surface of the first virtual object based on a first ray casting of the first virtual object, wherein the first ray casting includes straight lines through the 3D scene volume which collide with the first and second virtual object, wherein the first ray casting is in a direction from outside the scene volume towards the inside of the scene volume;
determining a location of a second surface point on a surface of the second virtual object based on a second ray casting of the second virtual object, wherein the second ray casting is in a direction from inside the scene volume to outside the scene volume, and wherein the second surface point has a desired positional relationship with respect to the first surface point, wherein a desired spatial relationship with respect to an inner surface of the 3D model of the mask sits flush with the surface of the 3D model of the user's head;

determining a relative position between the location of the first surface point and the location of the second surface point; and adjusting the location of the second surface point based on the relative position.

2. The method as claimed in claim 1, wherein adjusting the location of the second surface point comprises adjusting the location of the second virtual object.

3. The method as claimed in claim 1, wherein the steps of the method are repeated for a plurality of surface points on the first virtual object and a corresponding plurality of surface points on the second virtual object.

4. The method as claimed in claim 3, wherein adjusting the location of the second surface point comprises deforming the second virtual object based on the adjusted location of the second surface point.

5. The method as claimed in claim 4, wherein deforming the second virtual object comprises adjusting a location of an additional second surface point based on the adjusted location of the second surface point of the plurality of second surface points.

6. The method as claimed in claim 1, wherein the 3D model of a mask comprises one or more of:
a continuous positive airway pressure (CPAP) mask;
a medical sensory device;
a hearing aid;
a neck brace;
a piece of dental equipment, such as braces;
a piece of eyewear, such as glasses;
a pair of headphones;
a virtual reality headset;
a visualization of a post operation scar; and
an implant.

7. The method as claimed in claim 1, wherein the method comprises performing a preliminary alignment of the first virtual object and the second virtual object.

8. The method as claimed in claim 1, wherein the method further comprises:
deforming the first virtual object; and
deforming the second virtual object based on the deformation of the first virtual obj-ect.

9. A non-transitory computer readable medium storing therein a program that when executed by a computer performs the prescribed steps as recited in claim 1.

10. A system for aligning a first virtual object with a second virtual object, wherein the second virtual object is different from the first virtual object, within a scene volume in a three dimensional (3D) virtual space in which the first 3D virtual object and the second 3D virtual object exist and which defines a coordinate system that gives each of the virtual objects their locations, the system comprising:
a scanner adapted to generate a 3D model of a user's head based on a scan of the user's head; and
a processor adapted to:
receive the 3D model of the user's head from the scanner as the first virtual object, and wherein the second virtual object comprises a 3D model of a mask to be worn by the user;
determine a location of a first surface point on a surface of the first virtual object based on a first ray casting of the first virtual object, wherein the first ray casting includes straight lines through the 3D scene volume which collide with the first and second virtual object, wherein the first ray casting is in a direction from outside the scene volume towards the inside of the scene volume;
determine a location of a second surface point on a surface of the second virtual object based on a second ray casting of the second virtual object, wherein the second ray casting is in a direction from inside the scene volume to outside the scene volume, and wherein the second surface point has a desired positional relationship with respect to the first surface point, wherein a desired spatial relationship with respect to an inner surface of the 3D model of the mask sits flush with the surface of the 3D model of the user's head;
determine a relative position between the location of the first surface point and the location of the second surface point; and
adjust the location of the second surface point based on the relative position.

11. The system as claimed in claim 10, wherein the system further comprises a display adapted to display the scene volume to a user.

* * * * *